United States Patent [19]

Carson

[11] 3,998,844
[45] Dec. 21, 1976

[54] UNCATALYZED AROYLATION OF 1-ALKYLPYRROLE-2-ACETIC ACID DERIVATIVES

[75] Inventor: John Robert Carson, Norristown, Pa.

[73] Assignee: McNeil Laboratories, Incorporated, Ft. Washington, Pa.

[22] Filed: June 2, 1975

[21] Appl. No.: 583,065

[52] U.S. Cl. .................. 260/326.47; 260/326.2; 260/326.5 J; 260/326.55; 260/326.5 SM; 260/326.62; 260/326.35; 424/274
[51] Int. Cl.² .................................. C07D 207/32
[58] Field of Search ............... 260/326.5 J, 326.47, 260/326.5 S, 326.5 SM, 326.35

[56] References Cited

UNITED STATES PATENTS 3,752,826  8/1973  Carson .................. 260/326.5 X

OTHER PUBLICATIONS

Oddo, Ber. 47:2427–32 (1914).
Treibs et al., *Liebigs. Ann. Chem.* 721:105–15 (1969).

*Primary Examiner*—Nicholas S. Rizzo
*Assistant Examiner*—Mary C. Vaughn
*Attorney, Agent, or Firm*—Salvatore R. Conte

[57] ABSTRACT

A process of aroylating 1-alkylpyrrole-2-acetic acid esters and nitriles without employing the usual Friedel-Crafts of catalyst.

11 Claims, No Drawings

UNCATALYZED AROYLATION OF 1-ALKYLPYRROLE-2-ACETIC ACID DERIVATIVES

BACKGROUND OF THE INVENTION:

Several experimental problems are encountered in attempts to aroylate N-substituted pyrroles in the α-position which prevent high yields from being obtained. One such problem relates to the resulting alpha- and beta-isomer distribution of aroylated products. It is well known that electrophilic attack occurs more readily at the alpha- than at the beta-position of heteroaromatic 5-membered rings with one heteroatom. However, among such heterocycles, pyrroles have been reported [see Int. J. Sulfur Chem., C, 7, 64 (1972)] as giving the poorest ratio of α-isomer to β-isomer in electrophilic substitution reactions (furan> thiophene>>pyrrole).

Another problem relates to the use of acylation catalysts. Coordination of the pyrrole nitrogen with Lewis acids generally used as catalysts in a Friedel-Crafts type of reaction hinders the reaction. Furthermore, use of stronger Lewis acid catalysts, such as aluminum chloride, can induce polymerization of pyrroles. While examples of uncatalyzed acylations of N-substituted pyrroles with aliphatic acylating agents are known [e.g., see Ber. 47, 2427 (1910); Liebigs. Ann. Chem., 721, 105 (1969)], their reaction with aromatic acylating agents in the absence of catalyst has not been reported. Aroylation of N-unsubstituted pyrroles have been carried out using bases [e.g., see Liebigs. Ann. Chem., 724, 137 (1969) and 733, 27 (1970)]. The base acts by extracting a proton from the ring nitrogen and in such reactions, the pyrrole anion is the reactive intermediate. This type of reactivity, however, is not possible when the nitrogen atom bears a substituent.

The aroylation of 1-alkylpyrrole-2-acetic acid derivatives through a Friedel-Crafts type of reaction with $AlCl_3$ catalysts has been described in U.S. Pat. No. 3,752,826. However, low yields and formation of substantial quantities of the unwanted beta-isomer are typical of this reaction [see J. Med. Chem., 14, No. 7, 647 (1971)].

The non-catalyzed process of this invention constitutes an improvement in making the α-aroylated pyrroles of formula (I) over the conventional catalyzed methods. Not only are economic savings realized by elimination of the catalyst, but improved yields of product (I) are obtained substantially free of the corresponding β-aroyl isomers.

DESCRIPTION OF THE INVENTION

The present invention provides a process for preparing the 5-aroyl-1-loweralkylpyrrole-2-acetic acid derivatives of formula (I), which derivatives have anti-inflammatory activity (see U.S. Pat. No. 3,752,826):

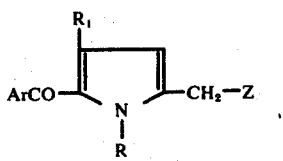

wherein R is loweralkyl; $R_1$ is a member selected from the group consisting of hydrogen and loweralkyl; Z is a member selected from the group consisting of CN and COO(loweralkyl); and Ar is a member selected from the group consisting of phenyl, thienyl, nitrophenyl, methylthiophenyl, trifluoromethylphenyl and phenyl substituted with from one to three substituents each selected from the group consisting of loweralkyl, loweralkoxy and halo; provided that when said $R_1$ is loweralkyl then said Z is COO(loweralkyl).

As used herein, "loweralkyl" and "loweralkoxy" may be straight or branch chained saturated hydrocarbons having from 1 to about 5 carbon atoms, such as, for example, methyl, ethyl, propyl, isopropyl, butyl, pentyl and the like alkyls, and the corresponding alkoxy such as methoxy, ethoxy, isopropoxy, etc., and the term halo is generic to chloro, bromo, fluoro and iodo.

According to the subject invention, an aroyl chloride of formula (II), wherein Ar is as previously described, is used as the acylating agent to react with 1-loweralkylpyrrole-4-$R_1$-2-acetic acid derivative of formula (III), wherein R, $R_1$ and Z are as previously described, in an aprotic organic solvent in the absence of catalyst at a temperature sufficient to make the aroylation proceed at a convenient rate.

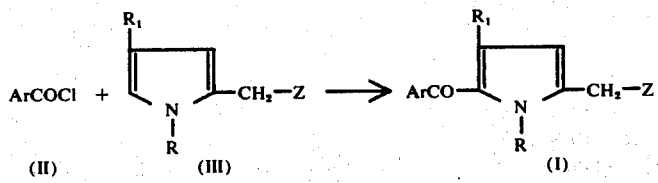

Typical of the aprotic solvents which may be utilized are aromatic hydrocarbons such as, for example, benzene, toluene, xylene, p-cymene and the like; substituted aromatic hydrocarbons such as, for example, chlorobenzene, dichlorobenzene, nitrobenzene, benzonitrile and the like; paraffins such as, for example, methyl cyclohexane, octane and the like, halocarbons such as, for example, methylene chloride, chloroform, tetrachloroethane, tetrachloroethylene and the like, ethers such as, for example, diethyl ether, diglyme and the like; ketones such as, for example, methyl ethyl ketone, cyclohexanone and the like; esters such as ethyl butyrate and the like; nitroalkanes such as nitropropane and the like; carbon disulfide; and the like.

The temperature of the reaction depends on the reactivities of the aroyl chloride (II) and of the particular pyrrole precursor (III). For example, for those pyrrole precursors wherein $R_1$ is loweralkyl and Z is COO(loweralkyl), the aroylation will adequately proceed at ambient temperatures (20°–27° C) although elevated temperatures up to the refluxing temperature of the solvent may be employed to enhance the rate of reaction. Those pyrrole precursors wherein $R_1$ is hydrogen and Z is COO(loweralkyl) may be aroylated at a convenient reaction rate at temperatures ranging from 50° to 250°

C, and for those pyrrole precursors wherein $R_1$ is hydrogen and Z is CN, a convenient reaction rate will be found in the 80° to 300° range. Preferably, the α-aroylation reactions of this invention are run at a temperature of at least 50° C to higher reflux temperatures depending on the particular solvent employed.

The reaction may be carried out employing substantially equivalent quantities of reactants (II) and (III) although an excess of the acylating agent (II) may be used to ensure completion of the reaction. In such cases, where residual aroyl chloride is still present upon termination of the reaction, standard reagents may be employed, such as, for example, a base such as an alkali metal hydroxide, e.g., sodium or potassium hydroxide, or a diamine, e.g., N,N-dimethylaminoproplylamine, to react with the excess aroyl chloride and facilitate its separation from the desired product (I).

The uncatalyzed aroylation process of this invention surprisingly affords better yields of the product, 4-$R_1$-1-loweralkyl-5-aroylpyrrole-2-acetic acid ester or nitrile. Moreover, when $R_1$ is hydrogen, the usual alpha to beta ratio of product in acylation reactions, that is, the distribution of α-aroylated and β-aroylated isomers, is very greatly shifted in favor of the α-substituted product. For example, in the $AlCl_3$ catalyzed Friedel Crafts reaction of p-chlorobenzoyl chloride with 1-methylpyrrole-2-acetonitrile, a 21% yield of the α-product, 5-(p-chlorobenzoyl)-1-methylpyrrole-2-acetonitrile, is obtained and the ratio of this α-isomer to the corresponding β-isomer, 4-(p-chlorobenzoyl)-1-methylpyrrole-2-acetonitrile, is about 2.5:1; and in the similarly catalyzed reaction of p-toluoyl chloride with 1-methylpyrrole-2-acetonitrile, a 25% yield of the α-product, 5-(p-toluoyl)-1-methylpyrrole-2-acetonitrile, is obtained with an alpha to beta isomer ratio of 3.7:1 [see Carson et al., J. Med. Chem., 14, 646 (1971)]. In contrast, the uncatalyzed reaction of p-chlorobenzoyl chloride with 1-methylpyrrole-2-acetonitrile in refluxing xylene for about 24 hours affords 46% of the corresponding α-product with an α/β ratio of about 440:1; and the uncatalyzed reaction of p-toluoyl chloride with 1-methylpyrrole-2-acetonitrile in refluxing o-dichlorobenzene for about 4 hours affords 55% of the corresponding α-product with an α/β ratio of about 180:1.

In contrast to reported acylations of certain other heteroaromatic substrates using traces of Lewis acid catalysts [e.g., see Synthesis, Oct., 1972, p. 533; and J. Am. Chem. Soc., 69, 1012 (1947)], the addition of small amounts of such catalysts actually decreases the rate of aroylation of the subject pyrrole precursors (III), as shown in Example III.

The products (I) of the subject aroylation process may be subjected to hydrolysis in order to facilitate their isolation and recovery. For example, the esters may be hydrolyzed to the corresponding acids and the nitriles may be converted by partial hydrolysis to the corresponding amides and by full hydrolysis to the corresponding acids.

The following examples are intended to illustrate, but not to limit, the scope of the present invention. Unless otherwise stated, all parts are by weight.

EXAMPLE I

1-Methyl-5-p-tolyoylpyrrole-2-acetonitrile

A solution of 11.5 g (0.075 mole) of p-toluoyl chloride and 6.0 g (0.05 mole) of 1-methylpyrrole-2-acetonitrile in 30 ml of toluene is heated under reflux for 68 hrs. The reaction mixture is then cooled, poured into an aqueous solution of N,N-dimethylaminopropylamine and diluted with chloroform. The organic layer is separated, washed successively with dilute hydrochloric acid and brine, dried ($MgSO_4$), charcoaled and the solvent evaporated in vacuo. The residue is crystallized from methanol to give 5.8 g (49% yield) of a brownish solid, 1-methyl-5-p-toluoylpyrrole-2-acetonitrile, m.p. 103°–105° C. No significant amount of the corresponding 4-isomer is produced.

EXAMPLE II

Solutions of 7.0 g (0.045 mole) of p-toluoyl chloride and 3.6 g (0.029 mole) of N-methylpyrrole-2-acetonitrile are heated under reflux in 20 ml of each solvent indicated below. The initial rates of reaction are assayed after 6 hrs. by gas chromatography. The percentage conversions to 1-methyl-5-p-toluoylpyrrole-2-acetonitrile are shown in the table.

| Solvent | % Conversion |
| --- | --- |
| o-dichlorobenzene, b.p. 180° C. | 54 |
| 1,1,2,2-tetrachloroethane, b.p. 146° C. | 37 |
| p-cymene, b.p. 177° C. | 32 |
| xylene, b.p. 140° C. | 16 |
| diglyme, b.p. 161° C. | 30 |

EXAMPLE III

Solutions of 7.0 g (0.045 mole) of p-toluoyl chloride and 3.6 g (0.029 mole) of N-methylpyrrole-2-acetonitrile in 20 ml of o-dichlorobenzene are heated under reflux with 1% of each of the catalysts indicated below. After 6 hrs the initial rates of reaction are assayed by gas chromatography. The percentage conversion to 1-methyl-5-p-toluoylpyrrole-2-acetonitrile are shown in the table.

| Catalyst | % Conversion |
| --- | --- |
| none | 54 |
| $FeCl_3$ | 35 |
| $I_2$ | 16 |
| $ZnCl_2$ | 20 |
| $TiCl_4$ | 20 |
| $SnCl_4$ | 25 |

EXAMPLE IV

A solution of 30 g. of 1-methylpyrrole-2-acetonitrile and 60 g of p-toluoyl chloride in 200 ml of o-dichlorobenzene is refluxed under nitrogen for 4 hrs. The mixture is concentrated to near dryness, diluted with 250 ml. of methylene chloride, washed successively with an aqueous solution of dimethylaminopropylamine, dilute hydrochloric acid and potassium carbonate solution. Removal of the organic solvent leaves an oily residue which crystallizes in 80 ml of methanol to give 22.2 g (39%) of 1-methyl-5-(p-toluoyl)-pyrrole-2-acetonitrile. The methanol filtrate is concentrated and the residual oil is hydrolyzed to the amide by brief refluxing with aqueous ethanolic NaOH (10%). The separated solid is collected giving 10.1 g (16.4%) of 1-methyl-5-(p-toluoyl)-pyrrole-2-acetamide. Total yield = 55.4%.

EXAMPLE V

Ethyl 1,4-dimethyl-5-(p-nitrobenzoyl)pyrrole-2-acetate

A solution of 7.24 g (0.04 mole) of ethyl 1,4-dimethylpyrrole-2-acetate and 11.1 g (0.06 mole) of p-nitrobenzoyl chloride in 30 ml of ether under argon is stirred at room temperature in the dark for two days. The precipitate is collected by filtration. Recrystallization from isopropanol gives 11.2 g (85% yield) of ethyl 1,4-dimethyl-5-(p-nitrobenzoyl)pyrrole-2-acetate as yellow crystals, m.p. 148°–149° C.

EXAMPLE VI

Ethyl 5-(3,4-dichlorobenzoyl)-1,4-dimethylpyrrole-2-acetate

A solution of 3.6 g of ethyl 1,4-dimethylpyrrole-2-acetate and 8.3 g of 3,4-dichlorobenzoyl chloride in 20 ml of xylene is refluxed for 40 min and then chilled. The separated solid is collected by filtration and dried to give 5.6 g (80%) of ethyl 5-(3,4-dichlorobenzoyl)-1,4-dimethylpyrrole-2-acetate as white crystals, m.p. 92°–93.5° C.

EXAMPLE VII

To a solution of 15.4 g of p-toluoyl chloride and 32.5 g of stannic chloride in 100 ml. of a mixture of 1,2-dichloroethane and nitromethane (1:1), cooled to −20° C, is added 15.3 g of methyl 1-methylpyrrole-2-acetate over a period of 20 min. The resulting mixture is allowed to come to room temperature over a 2 hr. period with stirring. It is then treated with dilute hydrochloric acid solution, the layers are separated and the organic layer concentrated. GLC analysis of the residual oil indicates the presence of 6 g. of product (22% yield). From this oil a total of 4 g. (15%) of methyl 1-methyl-5-(p-toluoyl)pyrrole-2-acetate is isolated, m.p. 117°–118° C.

EXAMPLE VIII

A comparison of catalyzed versus non-catalyzed aroylations is presented in Table 1 below employing appropriate quantities of aroyl chlorides (II) and pyrrole precursors (III) under the shown conditions.

Table 1

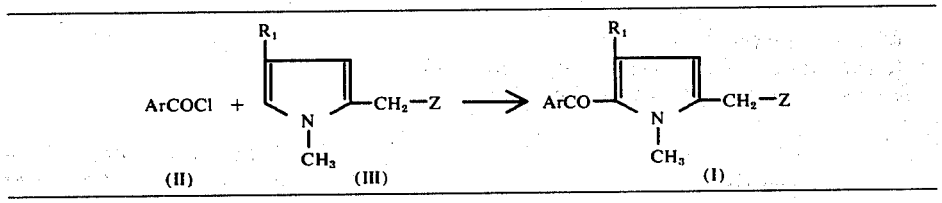

| Ar | $R_1$ | Z | Catalyst | Solvent | Temp. (°) | Time | (II) : (III) | Yield |
|---|---|---|---|---|---|---|---|---|
| p-Cl-Ph | H | CN | none | xylene | 140 | 24 hrs. | 2 : 1 | 46% |
|  |  |  | AlCl$_3$ | (ClCH$_2$)$_2$ | 25 → 83 | 20 mins. | 1 : 1 | 21% |
| p-Me-Ph | H | CN | none | toluene | 110 | 68 hrs. | 3 : 2 | 49% |
|  |  |  | AlCl$_3$ | (ClCH$_2$)$_2$ | 25 → 83 | 20 mins. | 1 : 1 | 25% |
| 2-thienyl | H | CN | none | xylene | 140 | 24 hrs. | 2 : 1 | 23% |
|  |  |  | AlCl$_3$ | (ClCH$_2$)$_2$ | 5 → 83 | 28 mins. | 1 : 1 | 21% |
| o-Cl-Ph | H | CN | none | xylene | 140 | 24 hrs. | 2 : 1 | 26% |
|  |  |  | AlCl$_3$ | (ClCH$_2$)$_2$ | 10 → 83 | 23 mins. | 1 : 1 | 10% |
| p-CF$_3$-Ph | H | CN | none | xylene | 140 | 18 hrs. | 3 : 2 | 56% |
|  |  |  | SnCl$_4$ | CH$_2$Cl$_2$ | −25 → 25 | 1 hr. | 1 : 1 | 10% |
| p-CH$_3$S-Ph | CH$_3$ | COOEt | none | xylene | 140 | 3 hrs. | 1.2 : 1 | 64% |
|  |  |  | AlCl$_3$ | (ClCH$_2$)$_2$ | 25 | 2 hrs. | 1 : 1 | 12% |
| p-MeO-Ph | H | COOMe | none | xylene | 140 | 18 hrs. | 1.5 : 1 | 64% |
|  |  |  | AlCl$_3$ | CH$_2$Cl$_2$ | 5 | 30 mins. | 1 : 1 | 7% |
| p-NO$_2$-Ph | H | COOEt | none | CHCl$_3$ | 64 | 24 hrs. | 3 : 2 | 40% |
|  |  |  | AlCl$_3$ | CH$_2$Cl$_2$ | 15 → 25 | 30 mins. | 1 : 1 | 19% |
| p-Me-Ph | H | COOMe | none | xylene | 140 | 5 hrs. | 2.4 : 1 | 92% |

Table 1-continued

ArCOCl + (pyrrole with $R_1$, $CH_2$-Z, N-$CH_3$) → ArCO-(pyrrole with $R_1$, $CH_2$-Z, N-$CH_3$)
(II)  (III)  (I)

| Ar | $R_1$ | Z | Catalyst | Solvent | Temp. (°) | Time | (II) : (III) | Yield |
|---|---|---|---|---|---|---|---|---|
| | | | SnCl$_4$ | (ClCH$_2$)$_2$ | $-20 \longrightarrow 25$ | 2 hr, 20 min. | 1 : 1 | 22% |
| Ph | Me | COOEt | none | xylene | 140 | 3 hrs. | 1.2 : 1 | 71% |
| | | | AlCl$_3$ | (ClCH$_2$)$_2$ | 25 | 2 hrs. | 1 : 1 | 24% |
| p-F-Ph | Me | COOEt | none | xylene | 140 | 4 hrs. | 1.1 : 1 | 79% |
| | | | AlCl$_3$ | (ClCH$_2$)$_2$ | 25 | 2 hrs. | 1 : 1 | 25% |
| p-Cl-Ph | Me | COOEt | none | xylene | 140 | 20 mins. | 2 : 1 | 87% |
| | | | AlCl$_3$ | (ClCH$_2$)$_2$ | 25 | 2 hrs. | 1 : 1 | 19% |

What is claimed is:

1. The process of preparing 5-aroyl-1-loweralkylpyrrole-2-acetic acid derivatives of the formula:

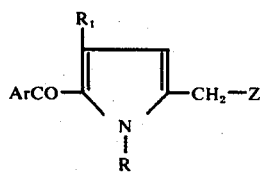

which comprises reacting an aroyl chloride of the formula:

with a pyrrole of the formula:

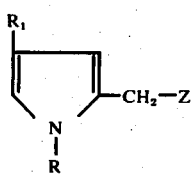

in an aprotic solvent in the absence of catalyst, wherein the foregoing formulas R is loweralkyl, $R_1$ is a member selected from the group consisting of hydrogen and loweralkyl, Z is a member selected from the group consisting of CN and COO(loweralkyl), and Ar is a member selected from the group consisting of phenyl, thienyl, nitrophenyl, methylthiophenyl, trifluoromethylphenyl and phenyl substituted with from one to three substituents each selected from the group consisting of loweralkyl, loweralkoxy and halo and wherein said reaction is carried out at a temperature in the range of from ambient temperature to the refluxing temperature of the solvent, provided that when $R_1$ in the reactant pyrrole is hydrogen, the reaction temperature is at least 50° C.

2. The process of preparing 5-aroyl-1-loweralkylpyrrole-2-acetic acid derivatives of the formula:

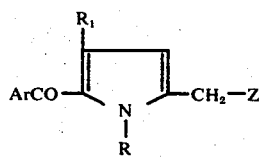

which comprises reacting an aroyl chloride of the formula:

with a pyrrole of the formula:

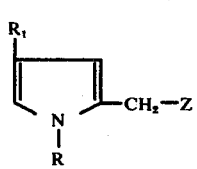

in an aprotic solvent at a temperature of from 50° C to the refluxing temperature of the solvent in the absence of catalyst, wherein the foregoing formulas R is loweralkyl, $R_1$ is a member selected from the group consisting of hydrogen and loweralkyl, Z is a member selected from the group consisting of CN and COO(loweralkyl), and Ar is a member selected from the group consisting of phenyl, thienyl, nitrophenyl, methylthiophenyl, trifluoromethylphenyl and phenyl substituted with from one to three substituents each selected from the group consisting of loweralkyl, loweralkoxy and halo.

3. The process of preparing 5-aroyl-1-loweralkylpyrrole-2-acetic acid esters of the formula:

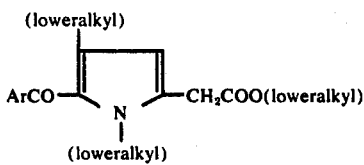

which comprises reacting an aroyl chloride of the formula:

ArCOCl with a pyrrole of the formula:

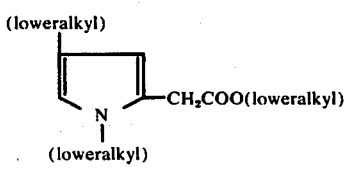

in an aprotic solvent at ambient temperature to the refluxing temperature of the solvent in the absence of catalyst, wherein Ar is a member selected from the group consisting of phenyl, thienyl, nitrophenyl, methylthiophenyl, trifluoromethylphenyl and phenyl substituted with from one to three substituents each selected from the group consisting of loweralkyl, loweralkoxy and halo.

4. The process of preparing 5-aroyl-1-loweralkylpyrrole-2-acetic acid esters of the formula:

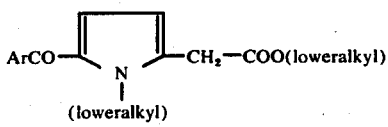

which comprises reacting an aroyl chloride of the formula:

ArCOCl with a pyrrole of the formula:

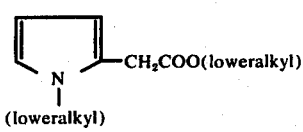

in an aprotic solvent at 50° to 250° C in the absence of catalyst, wherein Ar is member selected from the group consisting of phenyl, thienyl, nitrophenyl, methylthiophenyl, trifluoromethylphenyl and phenyl substituted with from one to three substituents each selectd from the group consisting of loweralkyl, loweralkoxy and halo.

5. The process of preparing 5-aroyl-1-loweralkyl-pyrrole-2-acetic acid nitriles of the formula:

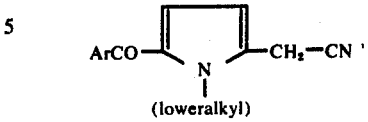

which comprises reacting an aroyl chloride of the formula:

ArCOCl with a pyrrole of the formula:

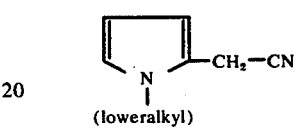

in an aprotic solvent at 80° to 300° C in the absence of catalyst, wherein Ar is a member selected from the group consisting of phenyl, thienyl, nitrophenyl, methylthiophenyl, trifluoromethylphenyl and phenyl substituted with from one to three substituents each selected from the group consisting of loweralkyl, loweralkoxy and halo.

6. The process of preparing 1-methyl-5-p-toluoylpyrrole-2-acetonitrile which comprises reacting p-toluoyl chloride with 1-methylpyrrole-2-acetonitrile in an aprotic solvent in the absence of catalyst at 80° to 300° C.

7. The process of preparing 1-methyl-5-p-toluoylpyrrole-2-acetonitrile which comprises reacting p-toluoyl chloride with 1-methylpyrrole-2-acetonitrile in an aromatic hydrocarbon solvent under reflux in the absence of catalyst.

8. The process of preparing ethyl 1,4-dimethyl-5-(p-nitrobenzoyl)pyrrole-2-acetate which comprises reacting p-nitrobenzoyl chloride with ethyl 1,4-dimethylpyrrole-2-acetate in an aprotic solvent at ambient temperature to the refluxing temperature of the solvent in the absence of catalyst.

9. The process of preparing ethyl 1,4-dimethyl-5-(p-nitrobenzoyl)pyrrole-2-acetate which comprises reacting p-nitrobenzoyl chloride with ethyl 1,4-dimethylpyrrole-2-acetate in ether at ambient temperature in the absence of catalyst.

10. The process of preparing ethyl 5-p-chlorobenzoyl-1,4-dimethylpyrrole-2-acetate which comprises reacting p-chlorobenzoyl chloride with ethyl 1,4-dimethylpyrrole-2-acetate in an aprotic solvent at ambient temperature to the refluxing temperature of the solvent in the absence of catalyst.

11. The process of preparing ethyl 5-p-chlorobenzoyl-1,4-dimethylpyrrole-2-acetate which comprises reacting p-chlorobenzoyl chloride with ethyl 1,4-dimethylpyrrole-2-acetate in ether at ambient temperature in the absence of catalyst.

* * * * *